(12) United States Patent
Oates et al.

(10) Patent No.: US 6,168,938 B1
(45) Date of Patent: Jan. 2, 2001

(54) METHOD FOR THE PRODUCTION OF THROMBIN

(75) Inventors: Adrian Malcolm Oates; Malgorzata Kupczyk; Jerry Kanellos, all of Victoria (AU)

(73) Assignee: CSL Limited, Victoria (AU)

( * ) Notice: Under 35 U.S.C. 154(b), the term of this patent shall be extended for 0 days.

(21) Appl. No.: 09/000,228

(22) PCT Filed: Jul. 22, 1996

(86) PCT No.: PCT/AU96/00457

§ 371 Date: Jan. 23, 1998

§ 102(e) Date: Jan. 23, 1998

(87) PCT Pub. No.: WO97/04081

PCT Pub. Date: Feb. 6, 1997

(30) Foreign Application Priority Data

Jul. 24, 1995 (AU) .................................................... PN4369

(51) Int. Cl.⁷ ...................................................... C12N 9/74
(52) U.S. Cl. ............................................................. 435/214
(58) Field of Search ............................................... 435/214

(56) References Cited

U.S. PATENT DOCUMENTS 5,723,123 * 3/1998 Karges et al. ..................... 424/94.65

FOREIGN PATENT DOCUMENTS

81/02105   8/1981   (WO) .

OTHER PUBLICATIONS

JP A 7–308190 (The Green Gross Corp) Nov. 28, 1995.
Middleton et al., A Therapeutic concentrate of Coagulation Factors II, IX and X From Citrated, Factor VIII–Vox Sang, vol. 24, pp. 441–456 (1973.

* cited by examiner

Primary Examiner—Herbert J. Lilling
(74) Attorney, Agent, or Firm—Foley & Lardner

(57) ABSTRACT

A method for the preparation of thrombin from a prothrombin-containing material is characterised in that the prothrombin-containing material is an activated prothrombin complex concentrate ActPCC fraction, which is contacted with divalent cations to convert the prothrombin to thrombin.

8 Claims, 3 Drawing Sheets

METHOD FOR THE PRODUCTION OF THROMBIN

This application is a 371 of PCT/AU96/00456 filed Jul. 22, 1996.

FIELD OF THE INVENTION

This invention relates to the preparation of thrombin by the activation of prothrombin. Thrombin prepared in accordance with this invention may be used in a fibrin glue kit, as a topical agent in its own right for therapeutic use in humans, or as a diagnostic reagent.

BACKGROUND OF THE INVENTION

Thrombin is a serine protease representing the active form of the coagulation factor, prothrombin. Its most studied role is its ability to convert soluble fibrinogen into an insoluble fibrin clot, thereby stemming the flow of blood from an injured blood vessel. Thrombin also cleaves and activates factor XIII to factor XIIIa which serves to stabilise the formed fibrin clot even further (Furie, 1991).

The conversion of prothrombin to thrombin can be performed in many different ways. According to the classic description of coagulation, prothrombin is converted to thrombin by coagulation factor Xa in the presence of cofactors factor Va, phospholipid and calcium chloride (Esmon, 1974). Various snake venoms also cleave prothrombin to form thrombin, examples being the venom of the Taipan snake *Oxyuranus scutellus* (Owen and Jackson, 1973), the Tiger snake *Notechis scutatus* (Jobin and Esnouf, 1966), and the saw-scaled viper *Echis carinatus* (Franza, 1975). However, none of these have been used commercially in the production of thrombin for clinical application.

Factor Xa, required for classic prothrombin activation, can be generated in many ways. The Intrinsic Pathway of Coagulation suggests that factor X is converted to factor Xa when incubated with factor IXa in the presence of cofactors factor VIIIa, phospholipid and calcium chloride. The Extrinsic Pathway of Coagulation is initiated by the exposure of tissue factor (containing thromboplastin) to factor VII in the presence of calcium chloride. This serves to activate factor VII to factor VIIa which in turn converts factor X to factor Xa. Both forms of factor Xa then activate prothrombin as described above (Furie, 1991) There are no reports of commercial preparations of thrombin exploiting features of the Intrinsic Pathway for generation of factor Xa, however there are a number of reports of exploitation of the Extrinsic Pathway to generate sufficient factor Xa to subsequently activate prothrombin by adding thromboplastin to the prothrombin-containing starting material (see, for example, Japanese Patent Publications Nos 63290829 and 2019400 in the name of Green Cross Corporation, and European Patent Publication No. 443724 in the name of Baxter International Inc.) Factor Xa can also be formed by incubating factor X with Russell's Viper venom (RVV) in the presence of calcium chloride (Kisiel, 1976). This approach has been used commercially (Bio-Products Laboratories) for the preparation of thrombin as a diagnostic reagent. However, the need to demonstrate the absence of soluble RVV in the final product would pose difficulties with its registration as a therapeutic agent.

A crude preparation of thrombin has been manufactured by the present applicant using thrombogenic discard fractions from the Prothrombin Complex Concentrate (PCC) manufacturing process, in which the prothrombin has been converted to thrombin by incubating the starting material with human placenta-derived thromboplastin in the presence of calcium chloride. A limitation of this method has been controlling the quality control of the placental thromboplastin. As a diagnostic product, this has not posed such a problem, however, for clinical use, clinical registration requires strict safeguards which have not been practical to introduce.

Commercial preparations of thrombin are of particular value as therapeutic agents as well as in diagnostic applications. In particular, thrombin may be used to promote coagulation as a topical agent (in either liquid or powderform) or incorporated into wound dressings. Furthermore, thrombin may be used as a component of a fibrin glue kit in which, in use, thrombin and fibrinogen factor XIII are combined for application to surgical incisions and other fresh wounds to replace the use of sutures, particularly during surgery on delicate tissues.

In work leading to the present invention, the present inventors have developed a method of activation of prothrombin to thrombin which does not require the use of thromboplastin, either human or any other species. Furthermore, the method of the present invention is characterised by the use of a fraction from the Prothrombin Complete Concentrate (PCC) prepared by the published method of Middleton et al, 1973 which has normally been discarded. As a result, the present invention provides a thrombin product which can be produced economically on a commercial scale.

SUMMARY OF THE INVENTION

According to the present invention, there is provided a method for the preparation of thrombin from a prothrombin-containing material, characterised in that the prothrombin-containing material is an Activated Prothrom bin Complex Concentrate (ActPCC) fraction as described hereinafter, and said ActPCC fraction is contacted with divalent cations in order to convert prothrombin in said fraction to thrombin. As mentioned previously, it has been found that when thrombin is prepared from the ActPCC fraction in accordance with this invention, the presence of thromboplastin is not required.

The "ActPCC fraction" which is used as the prothrombin-containing starting material in accordance with the invention comprises at least some of the thrombogenic fractions in the ascending or pre-peak material produced during the preparation of Prothrombin Complex Concentrate (PCC) by elution of the bound proteins from Cohn fraction I supematant from DEAE-cellulose resin. Further details of the ActPCC fraction, and the production thereof, are given in the detailed description and the Examples hereunder.

The present invention also extends to thrombin prepared by the method broadly described above, as well as to therapeutic and diagnostic preparations thereof. In addition, the invention extends to fibrin glue kits comprising thrombin produced by the method of this invention.

Preferably, the divalent cations used in the method of this invention are $Ca^{2+}$ ions, and conveniently $CaCl_2$ is used in the activation of the ActPCC fraction.

In another preferred aspect, it has been found that the optimum concentration of $Ca^{2+}$ ions for production of thrombin in accordance with this invention is in the range of 25 to 50 mM, more preferably from 35 to 50 mM, and most preferably at a concentration of about 40 mM. Furthermore, it has also been found that although the production of thrombin can be performed at temperatures in the range of 4° C. to 37° C., the optimum temperature does vary with $Ca^{2+}$ concentration. In particular, the optimum and hence preferred temperature is in the range of 22° C. to 25° C.

In a particularly preferred embodiment of this invention, the ActPCC fraction is treated with 40±5 mM $CaCl_2$ at 22–25° C. for a period of 4–5 hours.

Of course, after the treatment in accordance with this invention to convert the prothrombin to thrombin, the thrombin is recovered and purified by methods which are well-known in the art in order to produce a commercial concentrate which may, for example, be >90% pure thrombin.

Preferably, the further processing steps include a virus-inactivation step, such as a solvent/detergent treatment (for example by incubating the product with 0.3% TNBP/1% Tween 80 for 8–12 hours at 24° C.–26° C.), in order to produce a virus-safe thrombin concentrate. The virus-inactivated product may then be further treated for recovery of the thrombin by chromatography, for example with Heparin-agarose (such as Heparin-Sepharose) at a pH in the range of 6–8 (preferably pH 7.5), with elution of thrombin by NaCl, preferably at a NaCl concentration above 350 mM.

Throughout this specification, unless the context requires otherwise, the word "comprise", or variations such as "comprises" or "comprising", will be understood to imply the inclusion of a stated integer or group of integers but not the exclusion of any other integer or group of integers.

DETAILED DESCRIPTION OF THE INVENTION

A summary of an entire method of production of thrombin in accordance with the preferred aspects of the present invention is shown in Table 1.

TABLE 1

Summary of Thrombin production

Figure 1:
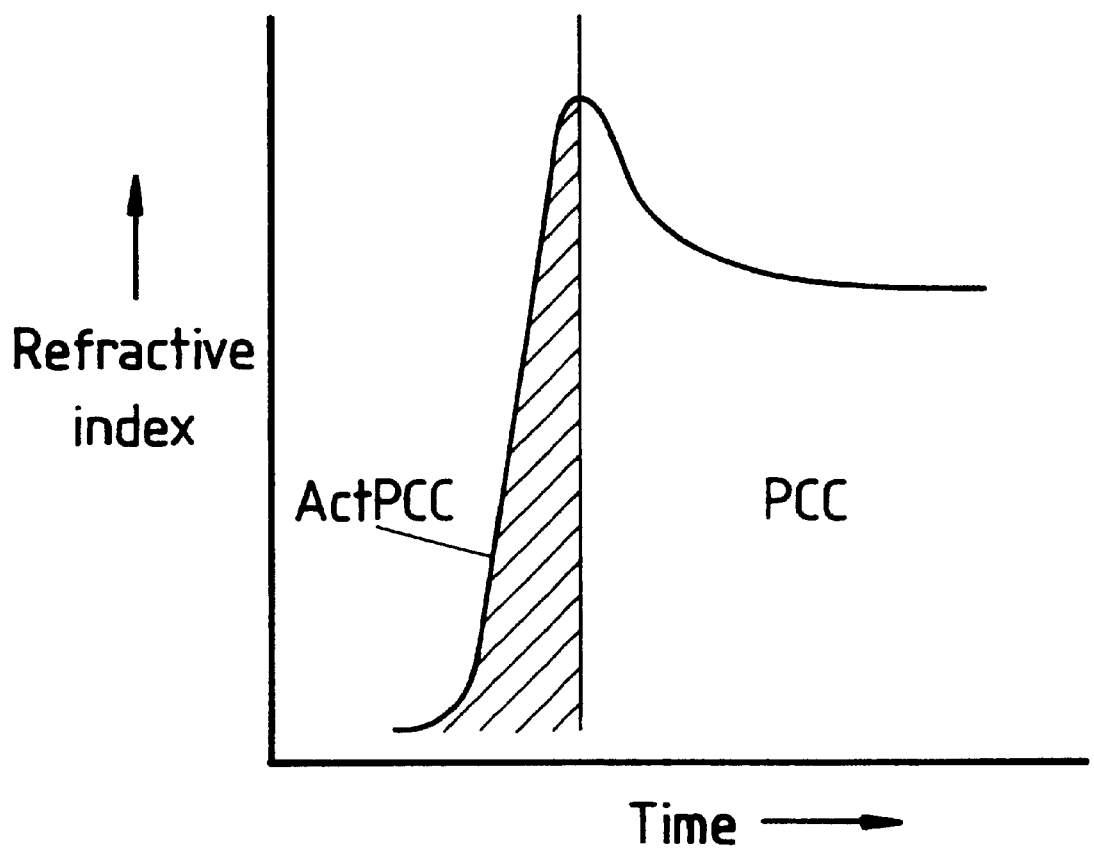
FIG. 1 shows the elution of ActPCC and PCC from an anion exchange column.

Plasma
↓
Cryosupernatant
↓
Fraction I supernatant
↓
PCC ← Activated PCC fractions
↓
Activation using $CaCl_2$
↓
Filtration/centrifugation
↓
Virus inactivation (solvent/detergent)
↓
pH/Conductivity adjustment
↓
Heparin-agarose chromatography
↓
Sephacryl S-100 chromatography
↓
Nanofiltration TABLE 1-continued Summary of Thrombin production ↓
Formulation
↓
Sterile filtration
↓
Dispensing
↓
Freezing
↓
Freeze-drying In general terms, in this preferred method a Prothrombin Complex Concentrate (PCC) is prepared according to the method as originally described by Middleton et al, 1973. Diluted Cohn fraction I supernatant is mixed batch-wise with DEAE-cellulose resin, centrifuged and the resin transferred into a chromatographic column. Unbound proteins are washed through the resin with bound proteins (including prothrombin) eluted with a higher salt buffer. The proteins eluting from the column are traced by refractive index monitoring with the ascending peak material collected as the starting material for prothrombin activation in accordance with the present invention. These fractions (ActPCC) contain activated coagulation factors and are normally discarded when preparing a Prothrombin Complex Concentrate, however, as described above, it has been found that this fraction is an ideal source of prothrombin for generation of thrombin. The descending peak is collected and used to manufacture a Prothrombin Complex Concentrate (PCC). The elution of the ActPCC and PCC fractions is shown in FIG. 1. Preferably, the ActPCC fraction is then incubated with an optimal level of calcium chloride at an optimal temperature range of 22–25° C. The method of this invention has been based on the in vitro thrombogenicity test as originally described by Sas et al, 1975 and Farrugia et al, 1989, which is used to detect thrombogenicity (degree of activation of the clotting system) by adding 37 mM calcium chloride at 37° C. and measuring the degree of thrombin generation.

Further features of the present invention are more fully described in the following Examples. It is to be understood, however, that this detailed description is included solely for the purposes of exemplifying the present invention, and should not be understood in any way as a restriction on the broad description of the invention as set out above.

EXAMPLE 1

This Example describes one specific method of prothrombin activation to generate thrombin in accordance with this invention.

1. Treatment with Anion Exchange Resin

Fraction I supernatant from the Cohn fractionation process is diluted to lower the ionic strength of the mixture. This is then mixed with DEAE-ellulose resin to adsorb Factor IX. The procedure is as follows:

(i) To the Fraction I supernatant, sterilised resin suspension is added in a quantity (measured in terms of wet DEAE resin) of 20 to 40 grams per litre of Fraction I supernatant.

(ii) Sufficient water is then added to adjust the temperature of the Fraction I supernatant:resin mixture to 2±2° C. and to dilute the mixture to a final volume of between 1.3 and 1.4 times the original volume of the Fraction I supernatant.

(iii) The resin mixture is stirred for not more than 2 hours at 2±2° C.

(iv) The loaded resin is separated by centrifugation at 2±2° C.

2. Preparation of Prothrombin Containing Fraction Bulk Solution 2.1 Washing of Adsorbed Resin Unbound proteins are removed from the DEAE resin by washing with Buffer W (see Table 2). Less than 1.2 litres of buffer per kg of resin are used for slurrying and washing. This and subsequent steps are carried out at ambient temperatures of not more than 30° C.

2.2 Elution of Adsorbed Resin

The Prothrombin containing fraction (ActPCC) is eluted from the resin by applying Buffer E (see Table 2) to the resin bed.

TABLE 2

Formulation of Buffers

| Component | Buffer W | Buffer E |
|---|---|---|
| Sodium acid phosphate BP | 0.03 | 0.03 |
| Sodium phosphate BP | 0.03 | 0.03 |
| Sodium citrate BP | 0.03 | 0.03 |
| Sodium chloride BP | 0 | 0.2 |
| pH | 6.5–6.7 | 6.3–6.5 |

2.3 Selection of Eluted Fractions

The eluting proteins are monitored using a refractive index meter. The ascending peak (ActPCC) is collected and used as a source of prothrombin as it contains activated coagulation factors unsuitable for Prothrombin Complex Concentrate manufacture but ideal as a source for thrombin generation. The peak and descending fractions (PCC) are also pooled and used for Prothrombin Complex Concentrate production.

The eluted pre-peak fractions (ActPCC) may either by frozen and/or clarified as described below.

2.4 Freezing of ActPCC Eluate (Optional step)

The pre-peak eluate is frozen rapidly to below −30° C. and stored at that temperature for not more than 6 months until required for further processing. Immediately before use the eluate is allowed to warm to room temperature (below 30° C.). The purpose of this optional step is to allow the manufacturing process to be halted and to provide the option of bulking two or more lots of eluate for preparation of thrombin.

3. Activation of Prothrombin Containing Fractions (ActPCC)

The required volume of ActPCC has calcium chloride added to a final concentration of 40±5 mM whilst mixing optimally at 22° C.–25° C. for up to 5 hours. At the end of this period, the crude thrombin solution is clarified by filtration/centrifugation, virus-inactivated and further processed into a thrombin concentrate as outlined in Table 1.

EXAMPLE 2

The Example describes the optimal temperature of thrombin generation by measurement of the rate and extend of thrombin formation over time at three different temperatures: 4° C., 22–25° C. and 37° C.

1. Buffer: 3.3 g/l $Na_2HPO_4.2H_2O$, pH 6.6

3.2 g/l $NaH_2PO_4.12H_2O$ 8.8 g/l $Na_3citrate.2H_2O$

2. Conditions: Prothrombinex (PTX) discard fractions were incubated at 4° C. (open squares), 22–25° C. (closed circles) and 37° C. (closed triangles) in the presence of 35 mM, 40 mM and 37 mM calcium chloride, respectively. The three different calcium chloride concentrations correspond to the optimal concentrations required for thrombin generation at the respective temperatures. Subsamples were removed over time and assessed for thrombin activity (chromogenic) and standardised against the International Standard for Thrombin (70/157).

Figure 2:
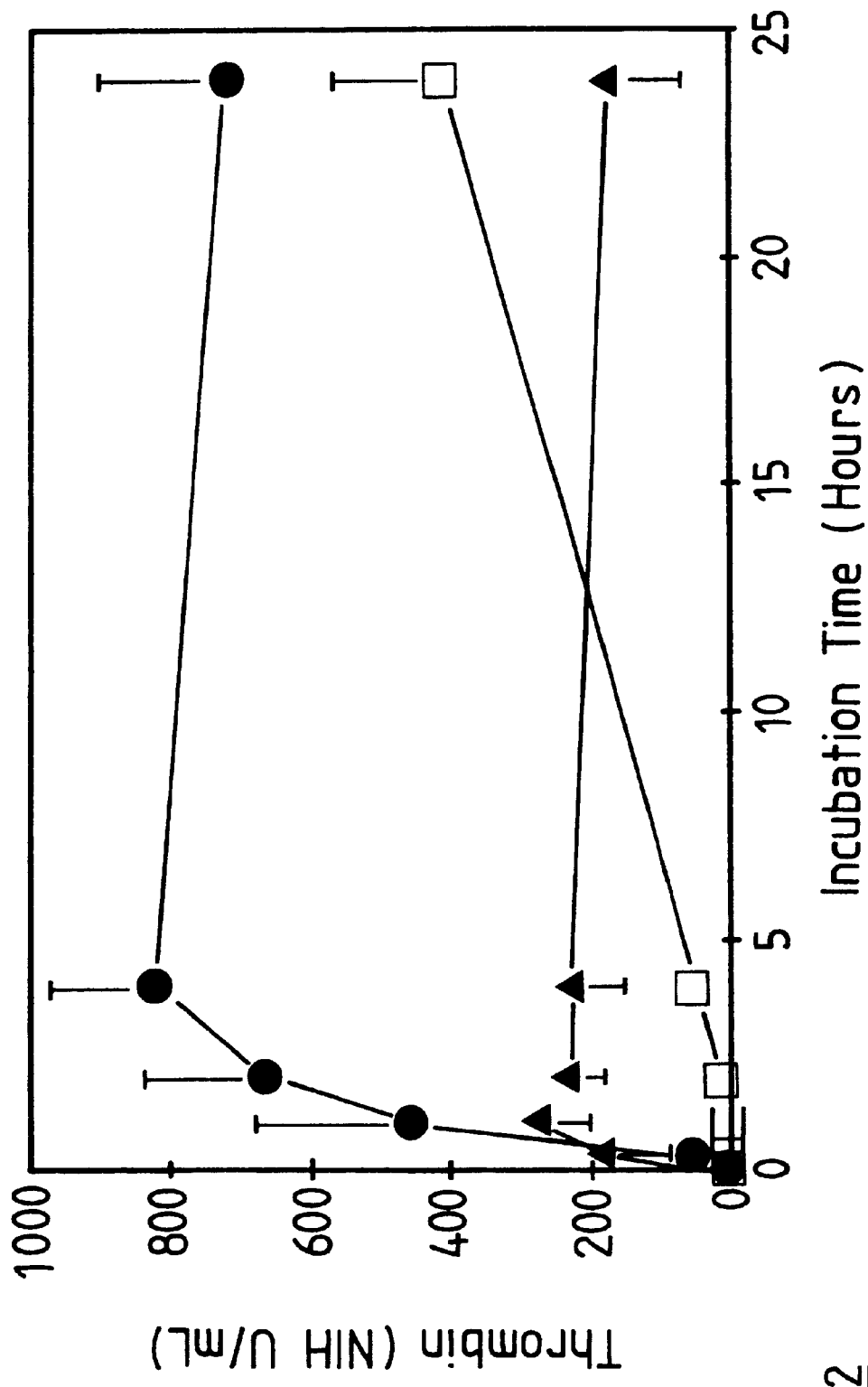
FIG. 2 shows the incubation of Prothrombinex discard fractions at 4° C. (open squares), 22–25° C. (closed circles) and 37° C. (closed triangles), in the presence of 35 mM, 40 mM and 37mM calcium chloride, respectively.

3. Conclusion: The results shown in FIG. 2 demonstrate that thrombin can be generated within the temperature range of 4° C. to 37° C., however, for optimal thrombin formation 22–25° C. should be used.

EXAMPLE 3

This Example describes the determination of the optimal calcium chloride concentration for PTX discard fraction activation of prothrombin to thrombin.

1. Buffer: 3.3 g/l $Na_2HPO_4.2H_2O$, pH 6.6

3.2 g/l $NaH_2PO_4.12H_2O$ 8.8 g/l $Na_3citrate.2H_2O$

2. Conditions: PTX discard fractions were incubated in the presence of increasing concentrations of calcium chloride (25–50 mM f.c.) for 4 hours at 22–25° C. At the end of this period, samples were assessed for thrombin generation and results expressed as International Units/mL.

Figure 3:
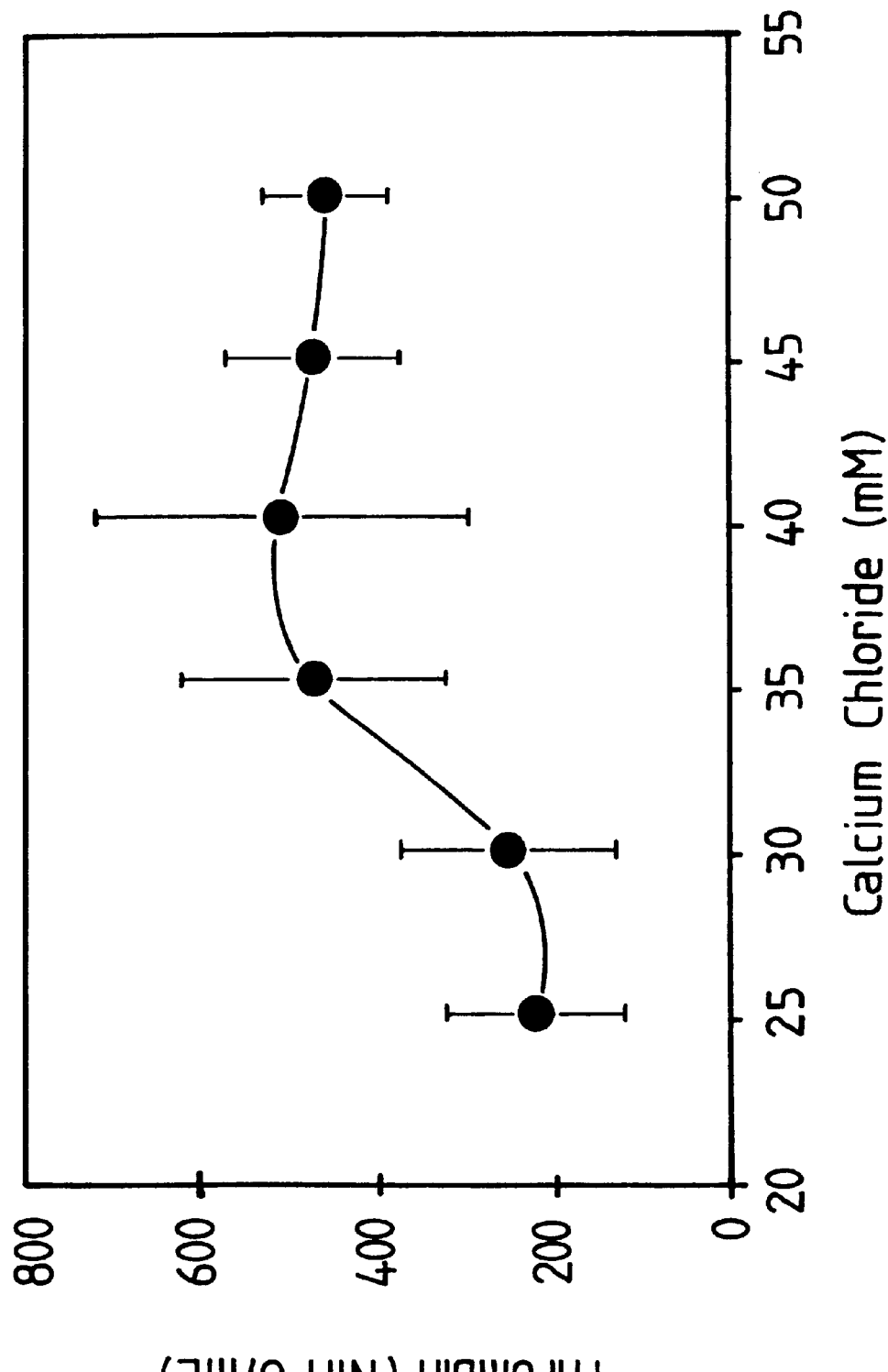
FIG. 3 shows a titration of calculations in generating thrombin.

3. Conclusion: The results shown in FIG. 3 demonstrate that thrombin can be generated in the presence of calcium chloride in the range of 25 to 50 mM final concentration, however, for optimal thrombin formation 40 mM final concentration should be used.

REFERENCES:

Esmon, C. T., Owen, W. G., Jackson, C. M. The conversion of prothrombin to thrombin. V. The activation of prothrombin by factor Xa in the presence of phospholipid. *J. Biol. Chem.* 249: 24, 7798–7807, 1974.

Farrugia, A., Oates, A., Spiers, D., Young, I., Herrington, R. A microtitre plate test for assessment of in vitro thrombogenicity in factor IX concentrates using a chromogenic substrate. Thrombosis Research. 53: 191–196, 1989.

Franza, R. B. Jnr, Aronson, D. L., Finlayson, J. B. Activation of human prothrombin by a procoagulant factor from the venom of *Echis cannatus*. Identification of a high molecular weight intermediate with thrombin activity. *J. Biol. Chem.* 250: 7056–7068, 1975.

Furie, B., Furie, B. C. The Molecular Basis of Blood Coagulation. Chapter 93, p 1213–1231 in Haematology, Basic Principles and Practice. Churchill Livingstone Inc. 1991.

Jobin, F., Esnouf, M. P. Coagulant activity of tiger snake (*Notechis scutatus scutatus*) venom. *Nature* 21: 873–875, 1966.

Kisiel, W., Hermodson, M. A., Davie, E. W. Factor X Activating Enzyme from Russell's Viper Venom: Isolation and Characterisation. *Biochemistry.* 15: 22, 4901–4906, 1976.

Middleton, S. M., Bennett, I. H., Smith, J. K. A therapeutic concentrate of coagulation factors II, IX and X from citrated, factor VII-depleted plasma. *Vox. Sang.* 24: 441–456, 1973.

Owen, W. G., Jackson, C. M. Activation of Prothrombin with *Oxyuranus scutellatus scutellatus* (Taipan Snake) venom. *Thrombosis Research*. 3: 705–714, 1973.

Sas, G., Owens, R. E., Smith, J. K., Middleton, S. M., Cash, J. D. In vitro spontaneous thrombin generation in human factor IX concentrates. *Br. J. Haemotol.* 31: 25–35, 1975.

What is claimed is:

1. A method for preparing thrombin from a prothrombin-containing material, comprising contacting the prothrombin-containing material with calcium ions at a concentration of from 25 to 50 mM, thereby converting said prothrombin to thrombin, wherein said prothrombin-containing material is an activated prothrombin complex concentrate (ActPCC) fraction, wherein said ActPCC fraction comprises at least one of the thrombogenic fractions in the ascending or pre-peak material obtained during preparation of prothrombin complex concentrate (PCC) by elution of bound proteins from Cohn fraction 1 supernatent from an ion exchange resin.

2. A method according to claim 1, wherein said contacting is done at a temperature in the range of from 4° C. to 37° C.

3. A method according to claim 2, wherein said contacting is done with 40±5mM $CaCl_2$ at 22° C. to 25° C. for a period of 4–5 hours.

4. A method according to claim 1, further comprising virus inactivation.

5. A method according to claim 1, further comprising recovering and purifying said thrombin.

6. A method according to claim 1, wherein the $Ca^{2+}$ ion concentration is between about 35 to 50 mM.

7. A method according to claim 2, wherein said contacting is done at a temperature from about 22° C. to 25° C.

8. A method according to claim 4, wherein said virus inactivation comprises treatment with solvent or detergent.

* * * * *